United States Patent [19]
Crotty et al.

[11] Patent Number: 5,972,314
[45] Date of Patent: Oct. 26, 1999

[54] SELF-TANNER COSMETIC COMPOSITIONS

[75] Inventors: Brian Andrew Crotty, Branford; Alexander Paul Znaiden, Trumbull; Anthony Johnson, Fairfield, all of Conn.

[73] Assignee: Chesebrough-Pond's USA Co., Division of Conopco, Inc., Greenwich, Conn.

[21] Appl. No.: 08/822,405

[22] Filed: Mar. 20, 1997

Related U.S. Application Data

[60] Provisional application No. 60/020,746, Jun. 28, 1996.
[51] Int. Cl.$^6$ .............................. A61K 7/42; A61K 7/00; A61K 31/74
[52] U.S. Cl. ..................... 424/59; 424/78.03; 424/400; 424/401
[58] Field of Search ................... 424/59, 78.03, 424/400, 401

[56] References Cited

U.S. PATENT DOCUMENTS

| | | | |
|---|---|---|---|
| 4,720,353 | 1/1988 | Bell | 252/309 |
| 4,742,142 | 5/1988 | Shimizu et al. | 528/15 |
| 4,980,167 | 12/1990 | Harashima et al. | 424/401 |
| 4,987,169 | 1/1991 | Kuwata et al. | 524/267 |
| 5,143,722 | 9/1992 | Hollenberg et al. | 424/63 |
| 5,266,321 | 11/1993 | Shukuzaki et al. | 424/401 |
| 5,280,019 | 1/1994 | Klimisch | 514/63 |
| 5,302,378 | 4/1994 | Crotty et al. | 424/59 |
| 5,387,417 | 2/1995 | Rentsch | 424/401 |

FOREIGN PATENT DOCUMENTS

| | | |
|---|---|---|
| 07267820 | 10/1995 | Japan . |
| 95/06078 | 3/1995 | WIPO . |
| 95/22960 | 8/1995 | WIPO . |
| WO 96/018374 | 6/1996 | WIPO . |

OTHER PUBLICATIONS

International Search Report Nov. 24, 1997.

Primary Examiner—Shelley A. Dodson
Attorney, Agent, or Firm—Milton L. Honig

[57] ABSTRACT

A self-tanning cosmetic product is provided for imparting a natural-appearing tan to skin. Besides the self-tanning agent, compositions of this invention will include a crosslinked non-emulsifying siloxane elastomer and a volatile siloxane.

7 Claims, No Drawings

SELF-TANNER COSMETIC COMPOSITIONS

This application claims benefit of Provisional application Ser. No. 60/020,746 filed Jun. 28, 1996.

BACKGROUND OF THE INVENTION

1. Field of the Invention

The invention concerns a cosmetic composition which rapidly imparts a tan similar in color to a natural suntan onto the skin.

2. The Related Art

Today there is a great health concern with natural tanning through sunlight. Ultraviolet radiation from the sun is considered to be a leading factor in causing skin cancer. Even if not lethal, ultraviolet radiation has been acknowledged as accelerating aging and wrinkling processes on the skin.

Beyond health concerns, there are obvious practical reasons against natural tanning. Foremost is the reason that in many areas of the globe and during all but summertime, there is insufficient sunlight available to accomplish a natural tan.

Based on the above considerations, there has been much interest in effectuating a tan through cosmetic means. Dihydroxyacetone (hereinafter known as DHA) has widely been utilized in cosmetics to accomplish self-tanning of the skin.

Although there has been great progress in self-tanning compositions, considerable further progress is needed to increase speed of coloration and achieve a coloration even closer to a natural tan.

Accordingly, it is an object of the present invention to provide a method and composition for self-tanning having improved rates of coloration, reduced streaking and imparting a more natural hue.

A further object of the present invention is to provide a method and composition for self-tanning which utilizes ingredients that impart good aesthetics and have an impeccable health safety profile.

Yet another object of the present invention is to provide a self-tanning composition which in emulsion form is stable for long term storage without phase separation.

Still another object of the present invention is to provide a composition for self-tanning which in emulsion form achieves a smooth emulsion break when rubbed into the skin.

Still another object of the present invention is to provide a composition for self-tanning which has improved skinfeel properties.

These and other objects of the present invention will become more readily apparent through the following summary, detailed discussion and Examples which follow.

SUMMARY OF THE INVENTION

A self-tanning composition is provided which includes:
(i) from 0.1 to 40% of a self-tanning agent;
(ii) from 0.1 to 30% of a crosslinked non-emulsifying siloxane elastomer; and
(iii) from 10 to 80% of a volatile siloxane.

DETAILED DESCRIPTION OF THE INVENTION

Now it has been discovered that a very rapid self-tanning with reduced streaking, improved color intensity and tone can be accomplished by delivering to the skin a self-tanning agent in combination with a crosslinked non-emulsifying siloxane elastomer and a volatile siloxane. Moreover, the composition can be formed into a highly stable emulsion. Improved skinfeel properties are also achieved with this combination of components.

Accordingly, a first essential element of the present invention is that of a self-tanning agent, especially a $C_3$–$C_{24}$ alpha-hydroxy alcohol or aldehyde in an amount from 0.1 to 40%, preferably from 1 to 20%, optimally between 2 and 15% by weight. The alpha-hydroxy alcohol or aldehyde may be selected from dihydroxyacetone, glucose, xylose, fructose, reose, ribose, pentose, arabinose, allose, tallose, altrose, mannose, galactose, lactose, sucrose, erythrose, cyclodextrin, glyceraldehyde and combinations thereof. Most preferred is dihydroxyacetone.

Crosslinked non-emulsifying siloxane elastomers are the second essential element of this invention. They will have an average number molecular weight in excess of 2,000, preferably in excess of 1,000,000 and optimally will range from 10,000 to 20 million. The term "non-emulsifying" defines a siloxane from which polyoxyalkylene units are absent. Advantageously the elastomers are formed from a divinyl monomer reacting with Si-H linkages of a siloxane backbone. Elastomer compositions are commercially available from the General Electric Company under product designation General Electric Silicone 1229 with proposed CTFA name of Cyclomethicone and Vinyl Dimethicone/Methicone Cross Polymer, delivered as 20–35% elastomer in a cyclomethicone carrier. A related elastomer composition under the CTFA name of Crosslinked Stearyl Methyl Dimethyl Siloxane Copolymer is available as Gransil SR-CYC (25–35% elastomer in cyclomethicone) from Grant Industries, Inc., Elmwood Park, N.J. The commercial products from General Electric and Grant Industries ordinarily are further processed by subjecting them to a high pressure (approximately 5,000 psi) treatment in a Sonolator with recycling in 10 to 60 passes. Sonolation achieves a resultant fluid with elastomer average particle size ranging from 0.2 to 10 micron, preferably 0.5 to 5 micron. Viscosity is best when ranging between 300 and 20,000 cps at 25° C. as measured by a Brookfield LV Viscometer (size 4 bar, 60 rpm, 15 sec.).

Amounts of the elastomer may range from 0.1 to 30%, optimally from 1 to 15%, most preferably from 3 to 10% by weight.

A third essential element to be incorporated into the compositions of this invention is that of a volatile siloxane. This material may be present in amounts from 10 to 80%, preferably from 20 to 60%, optimally from 30 to 50% by weight.

The term "volatile" refers to those materials having a measurable pressure at ambient conditions. Volatile polyorganosiloxanes useful herein may be cyclic or linear. Preferred cyclic silicones include polydimethylsiloxanes containing from about 3 to about 9 silicon atoms, preferably containing from about 4 to about 5 silicon atoms, generally known as cyclomethicones. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes, the preferable range being from 0.1 to 8 centistokes. Examples of silicone oils useful in the present invention include: Dow Corning 244, Dow Corning 245, Dow Corning 344, Dow Corning 345 and Dow Corning 200 (manufactured by the Dow Corning Corporation); Silicone 7207 and Silicone 7158 (manufactured by the Union Carbide Corporation); SF1202 (manufactured by General Electric).

Humectants may also be included as components of compositions according to the present invention. These humectants are polyhydric alcohols intended for moisturizing, reducing scaling and stimulating removal of built-up scale from the skin. Most important for the present invention, the polyhydric alcohols enhance skin colorization of the self-tanning agent. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin and mixtures thereof. Most preferably the humectant is glycerin. Amounts of humectant may range anywhere from 1 to 50%, preferably from 10 to 40%, optimally from 25 to 35% by weight.

Another optional component is that of an emollient which may be selected from hydrocarbons or esters. Petrolatum is the most preferred emollient conditioning agent. Other hydrocarbons that may be employed include mineral oil, polyolefins such as polydecene, and paraffins such as isohexadecane (e.g. Permethyl 99® and Permethyl 101®).

Ester emollients may be those selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikul oil and soybean oil.
2. Acetoglyceride esters, such as acetylated monoglycerides.
3. Ethoxylated glycerides, such as ethoxylated glyceryl monostearate.
4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
5. Alkenyl esters of fatty acids having 10 to 20 carbon atoms. Examples thereof include oleyl myristate, oleyl stearate, and oleyl oleate.
6. Ether-esters such as fatty acid esters of ethoxylated fatty alcohols.
7. Polyhydric alcohol esters. Ethylene glycol mono and di-fatty acid esters, diethylene glycol mono-and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.
8. Wax esters such as beeswax, spermaceti, myristyl myristate, stearyl stearate.

Cosmetic compositions of the present may either be anhydrous or aqueous emulsions. When anhydrous, the amount of water will be confined to range from 0 to 5%, preferably not above 2%, optimally not above 0.5% by weight. When the compositions of this invention are in emulsion form, the amount of water will range from 5 to 50%, preferably from 7 to 30%, optimally from 10 to 20% by weight. The emulsions may be of the oil-in-water, water-in-oil or duplex variety. Aqueous to oily phases can range in weight from 10:1 to 1:10, preferably from 1:1 to 1:5, optimally from 1:1 to 1:2.

Most preferable for the present invention are water-in-oil emulsions having a low internal (water) phase volume. These emulsions will normally consist essentially of self-tanning agent, elastomer, polyhydric alcohol, cyclomethicone and water. Anhydrous systems optimally will consist essentially of self-tanning agent, elastomer, petrolatum and cyclomethicone.

Beyond the basic components, other materials may be included depending upon the particular type of cosmetic composition sought. For instance, surfactants may be formulated into the compositions. These may be selected from nonionic, anionic, cationic or amphoteric emulsifying agents. They may range in amount anywhere from about 0.1 to about 20% by weight. Illustrative nonionic surfactants are alkoxylated compounds based on $C_{10}$–$C_{22}$ fatty alcohols and acids, and sorbitan. These materials are available, for instance, from the Shell Chemical Company under the Neodol trademark. Copolymers of polyoxypropylene-polyoxyethylene, sold by the BASF Corporation under the Pluronic trademark, are sometimes also useful. Alkyl polyglycosides available from the Henkel Corporation may also be utilized for purposes of this invention.

Anionic type surfactants include fatty acid soaps, sodium lauryl sulphate, sodium lauryl ether sulphate, alkyl benzene sulphonate, mono- and di-alkyl acid phosphates and sodium fatty acyl isethionate.

Amphoteric surfactants include such materials as dialkylamine oxide and various types of betaines (such as cocoamidopropyl betaine).

Preservatives can desirably be incorporated into the compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives are hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, imidazolidinyl urea, sodium dehydroxyacetate and benzyl alcohol. The preservatives should be selected having regard for the use of the composition and possible incompatibilities between the preservatives and other ingredients. Preservatives are preferably employed in amounts ranging from 0.01% to 2% by weight of the composition.

Minor adjunct ingredients may also be included such as fragrances, antifoam agents, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

This Example illustrates an anhydrous skin tanning composition. Components listed in the Table below are added together in a vessel at 60° C. and mixed with a homogenizing agitator. Thereafter they are subjected to sonolation at 800–1,000 psi for five to ten minutes. The resultant product is a non-greasy semi-solid with a very silky afterfeel and excellent self-tanning properties.

TABLE I

| COMPONENT | WEIGHT % |
| --- | --- |
| Petrolatum | 18.5 |
| GE 1229 | 30 |
| DC 344 Fluid ® | 41.5 |
| Dihydroxyacetone | 10 |

EXAMPLE 2

A water-in-oil emulsion of low internal phase is prepared in a manner similar to that of Example 1. The resultant tanning product will be fluid and highly penetrating when rubbed into the skin. It will exhibit an excellent smooth, silky afterfeel. The product will tan skin in a uniform, non-streaking manner.

TABLE II

| COMPONENT | WEIGHT % |
| --- | --- |
| Glycerin | 20 |
| GE 1229 | 20 |
| Water | 12 |
| DC 244 Fluid ® | 40 |
| Dihydroxyacetone | 8 |

EXAMPLE 3

This Example illustrates another anhydrous skin tanning composition according to the present invention. The formulation may be prepared in a manner essentially similar to that of Example 1 utilizing the components listed in the Table below. The resultant product will have a smooth, silky afterfeel and impart a tan of excellent color.

TABLE III

| COMPONENT | WEIGHT % |
| --- | --- |
| Petrolatum | 22 |
| Gransil SR-CYC | 43 |
| DC 244 Fluid ® | 33 |
| Cyclodextrin | 2 |

EXAMPLES 4–12

Illustrated in the Table below are a series of anhydrous and aqueous self-tanning emulsion formulations according to the present invention. These examples can be prepared in a manner similar to that described in Example 1.

TABLE IV

| COMPONENT | EXAMPLE NO. (WEIGHT %) | | | | | | | | |
| --- | --- | --- | --- | --- | --- | --- | --- | --- | --- |
| | 4 | 5 | 6 | 7 | 8 | 9 | 10 | 11 | 12 |
| Dihydroxyacetone | 5 | 10 | 15 | 10 | 10 | 10 | 2 | 20 | 30 |
| Petrolatum | 2 | 10 | 45 | — | — | — | — | 10 | 10 |
| Isohexadecane | 18 | 10 | — | — | — | — | — | — | — |
| Glycerin | — | — | — | 10 | — | — | 8 | — | 10 |
| Propylene Glycol | — | — | — | — | 10 | — | — | — | — |
| Polyethylene Glycol | — | — | — | — | — | 10 | — | — | — |
| Crosslinked Siloxane Elastomer | 30 | 20 | 10 | 10 | 10 | 10 | 10 | 15 | 20 |
| Water | — | — | — | 40 | 40 | 40 | 50 | 40 | 10 |
| Cyclomethicone | 45 | 50 | 30 | 30 | 30 | 30 | 30 | 15 | 20 |

EXAMPLE 13

Comparative performance characteristics were evaluated for a set of sunless tanner formulations listed in Table V.

TABLE V

| COMPONENT | EXAMPLE (WEIGHT %) | | |
| --- | --- | --- | --- |
| | A | B | C |
| DO 245 Fluid | 52.0 | 52.0 | 52.0 |
| EM-90 | 0.75 | 0.75 | 0.75 |
| Gransil SR-CYC | 8.0 | — | — |
| DC 200 (polydimethylsiloxane) | — | 8.0 | — |
| Trasil (cycloethoxymethicone) | — | — | 8.0 |
| Propylene Glycol | 25.0 | 25.0 | 25.0 |
| Water | 11.25 | 11.25 | 11.25 |
| Dihydroxyacetone | 3.0 | 3.0 | 3.0 |

Each of the samples were prepared in a manner similar to that described for Example 1. Sample A was an elegant cosmetic cream. Sample B was a liquid which separated upon standing. Sample C was a slightly viscous liquid which also separated upon standing.

Efficacy was tested by applying equal amounts of each sample over equivalent areas on the arms of a panelist. Approximately 1 cc of each formulation was applied over a 5 cm square area. Intensity, uniformity and tone were assessed after 24 hours. Results are reported in Table VI.

TABLE VI

| SAMPLE | COLOR INTENSITY | STREAKINESS | COLOR TONE |
| --- | --- | --- | --- |
| A | +++++ | – | Brown Excellent |
| B | + | – | Yellow Brown |
| C | ++++ | ––– | Yellow Brown |

The greater the number of (+) or (–) symbols the larger the respective beneficial or detrimental effect. As can be seen from Table VI, the best combination of properties was seen from Sample A. A very high degree of color intensity was achieved with excellent brown tone and acceptable uniformity. Sample exhibited a high degree of unacceptable streakiness.

The foregoing description and Examples illustrate select embodiments of the present invention. In light thereof, various modifications will be suggested to one skilled in the art, all of which are within the purview and spirit of this invention.

What is claimed is:

1. A self-tanning composition comprising:
   (i) from 0.1 to 40% of a self-tanning agent;
   (ii) from 0.1 to 30% of a crosslinked non-emulsifying siloxane elastomer; and
   (iii) from 10 to 80% of a volatile siloxane.

2. A composition according to claim 1 which is anhydrous.

3. The composition according to claim 1, further comprising from 5 to 50% by weight of water.

4. The composition according to claim 1 wherein the crosslinked non-emulsifying siloxane elastomer is formed from a divinyl monomer reacting with Si-H linkages of a siloxane backbone.

5. The composition according to claim 1 wherein the volatile siloxane is cyclomethicone.

6. A composition according to claim 1 wherein the self-tanning agent is selected from the group consisting of dihydroxyacetone, glucose, xylose, fructose, reose, ribose, pentose, arabinose, allose, tallose, altrose, mannose, galactose, lactose, sucrose, erythrose, cyclodextrin, glyceraldehyde and combinations thereof.

7. The cosmetic composition according to claim 1 wherein the self-tanning agent is dihydroxyacetone.

* * * * *